United States Patent
Gagnebien et al.

[11] Patent Number: 6,150,422
[45] Date of Patent: Nov. 21, 2000

[54] STABLE GELLED COMPOSITION CONTAINING LIPOPHILIC ACTIVE AGENTS SENSITIVE TO OXYGEN AND/OR WATER

[75] Inventors: Didier Gagnebien, Westfield, N.J.; Pascal Simon, Vitry Sur Seine, France

[73] Assignee: L'Oreal, Paris, France

[21] Appl. No.: 08/815,428

[22] Filed: Mar. 11, 1997

[30] Foreign Application Priority Data

Mar. 12, 1996 [FR] France .................... 96 03096

[51] Int. Cl.⁷ .................... A01N 31/04; A61K 31/04
[52] U.S. Cl. .................... 514/725; 514/782; 514/859; 424/78.02; 424/78.03
[58] Field of Search .................... 514/725, 782, 514/859; 424/78.02, 78.03

[56] References Cited

U.S. PATENT DOCUMENTS

| | | | |
|---|---|---|---|
| 4,169,945 | 10/1979 | DeGuia et al. | 536/114 |
| 4,826,828 | 5/1989 | Wilmott et al. | 514/63 |
| 5,728,371 | 3/1998 | Pinzon et al. | 424/59 |
| 5,728,372 | 3/1998 | Pinzon | 424/59 |

FOREIGN PATENT DOCUMENTS

| | | |
|---|---|---|
| 636800 | 5/1992 | Australia . |
| 0281360 | 9/1988 | European Pat. Off. . |
| 0481240A2 | 4/1992 | European Pat. Off. . |
| 0682936A1 | 11/1995 | European Pat. Off. . |
| 0 708 114 | 4/1996 | European Pat. Off. . |

OTHER PUBLICATIONS

WPIDS abstract, AN: 96–207276 [21], abstract of RD 384013A, Clarke, M.T. et al., 1996.

Goodman Gilman et al., "The Pharmacological Basis of Therapeutics"(6th Ed.), Macmillan Pub. Co., New York, pp. 1584–1585 and 1591, 1980.

Research Disclosure, No. 37807, Oct. 1995, p. 642. XP002018143 Majewicz et al: "Oil–Based Cosmetic and Therapeutic Compositions Containing Ethylguar".

*Primary Examiner*—Dwayne C. Jones
*Attorney, Agent, or Firm*—Oblon, Spivak, McClelland, Maier & Neustadt, P.C.

[57] ABSTRACT

A stable gelled composition, containing at least one lipophilic active agent sensitive to oxygen or to water or to both, and a solvent which contains, as gelling agent, at least one polysaccharide alkyl ether formed of units containing at least two different glycoside rings, each unit containing at least one hydroxyl group substituted with a saturated hydrocarbon alkyl group.

26 Claims, No Drawings

STABLE GELLED COMPOSITION CONTAINING LIPOPHILIC ACTIVE AGENTS SENSITIVE TO OXYGEN AND/OR WATER

BACKGROUND OF THE INVENTION

1. Field of the Invention

The present invention relates to a stable gelled composition containing lipophilic active agents sensitive to oxygen and/or water.

2. Description of the Background

Lipophilic active agents are known for their beneficial effects on the skin, especially upon topical application. Thus, retinol has, for a long time, been used in the treatment of acne. In addition, retinol is known to be effective in correcting damage induced either by age or by excessive intensive exposure to the sun.

Consequently, the effects of retinol on cell differentiation make it possible to envisage use thereof for effectively combating the appearance of normal and small wrinkles, skin dehydration, as well as roughness and/or stiffness of the skin. The activity of retinol in the regeneration of tissues make it an important compound in healing. A repeated application of cosmetic compositions containing retinol makes it possible to eliminate wrinkles, to smooth the skin, and to repair small cracks in the epidermis.

Due to these beneficial effects, attempts have been made for a long time to formulate retinol into cosmetically acceptable compositions, in a form stable for at least several months at room temperature.

Retinol-containing compositions which can be used in cosmetics are described, in particular, in U.S. Pat. 4,826,828 and WO-A-93/00085.

In U.S. Pat. No. 4,826,828, for example, water-in-oil emulsions containing retinol, a volatile silicone, as well as a solvent for retinol and volatile silicone are described. The preferred solvent is ethanol. It has now been demonstrated, however, that retinol is degraded in the presence of ethanol. To obtain the emulsion described therein, U.S. Pat. No. 4,826,828 describes the preparation of a solution containing retinol which is mixed at the time of use with a water-in-oil emulsion in order to avoid any degradation of the retinol. In addition, the use of antioxidant and of metal-chelating agent in the aqueous phase is indicated as being essential.

The stability of such compositions, as indicated by the owner of patent U.S. Pat. No. 826,828 on the packages of its products Bioadvance and Bioadvance 2000 described therein, does not exceed one month. Thus, the stability of retinol in this type of composition is inadequate for prolonged use. Consequently, frequent and expensive restocking is required.

In WO-A-93/00085, stabilization of retinol in cosmetic compositions, by the addition thereto of a stabilizing complex containing, in association, an antioxidant and a metal ion-chelating agent, is proposed. However, while the stability of retinol appears to be enhanced in such compositions (with 60% of the retinol remaining in the composition after three months storage at 40° C.), it is nevertheless true that the relative stability of retinol is due only to the presence of a large quantity of stabilizing chelating agents and antioxidants in the composition.

Numerous efforts have been made to eliminate, or at least reduce to the greatest extent possible, such stabilizers in cosmetic compositions containing retinol, while preserving its stability of the retinol in the composition to an acceptable degree for prolonged storage and use.

Additionally, many compounds other than retinol, such as derivatives of retinol, such as 0-carotene, retinol palmitate, retinol acetate, flavonoids and polyunsaturated fatty acids, exhibit similar inadequate stability for prolonged storage and use.

Thus, a need exists for gelled compositions containing lipophilic active agents sensitive to oxygen and/or waters, which are stable for prolonged storage and use.

SUMMARY OF THE INVENTION

Accordingly, it is an object of the present invention to avoid the above disadvantages and to provide a gelled composition containing a lipophilic active agent sensitive to oxygen and/or water, which is stable for prolonged storage and use.

Moreover, it is a particular object of the present invention to provide a stable gelled composition containing at least one lipophilic active agent sensitive to oxygen or water or both, and a solvent, which contains, as a gelling agent, at least one polysaccharide alkyl ether formed of units containing at least two different glycoside rings, each unit containing at least one hydroxyl group substituted with a saturated hydrocarbon alkyl chain.

DESCRIPTION OF THE PREFERRED EMBODIMENTS

The present invention generally relates to a stable gelled composition containing a lipophilic active agent sensitive to oxygen and/or to water, intended, in particular, for use in the cosmetic and/or dermatological fields. The present invention also relates to a use of this composition for treating the skin.

The present stable gelled composition contains at least one lipophilic active agent sensitive to oxygen and/or to water, and a solvent, which composition contains, as a gelling agent, at least one polysaccharide alkyl ether formed of units containing at least two different glycoside rings, each unit containing at least one hydroxyl group substituted with a saturated hydrocarbon alkyl chain.

By virtue of this specific gelling agent, the present composition is particularly stable over time and no significant degradation of the active agent sensitive to oxygen and/or to water, in particular retinol, is observed.

Accordingly, another important aspect of the present invention entails the use of a polysaccharide alkyl ether formed of units containing at least two different glycoside rings, each unit containing at least one hydroxyl group substituted with a saturated hydrocarbon alkyl chain, to stabilize a lipophilic active agent sensitive to oxygen and/or to water.

Active agents sensitive to oxygen and/or to water, which may be used in accordance with the present invention, are, for example, in addition to retinol, retinol derivatives such as β-carotene, retinol palmitate or acetate, flavonoids or polyunsaturated fatty acids.

According to a particular embodiment of the present invention, the polysaccharide alkyl ether has a molecular weight greater than about 100,000, and preferably greater than about 200,000. Each unit preferably contains from one to six, and more preferably, from two to four hydroxyl groups substituted with a saturated hydrocarbon alkyl chain.

The term "saturated hydrocarbon alkyl chain or group" is understood and used herein to mean a chain containing from 1 to about 24, preferably from 1 to about 10, and more preferably from 1 to about 5 carbon atoms. In particular, the alkyl chain or group may be methyl, ethyl, n-propyl, isopropyl, n-butyl, isobutyl, tert-butyl or n-pentyl.

The glycoside rings may be, for example, mannose, galactose, glucose, furanose, rhamnose or arabinose.

According to a preferred embodiment of the present invention, the polysaccharide alkyl ether is an alkyl ether of a gum and more particularly of a gum which is nonionic overall, that is to say which is practically without an ionic group. As appropriate gums, there may be mentioned, for example, guar gum whose unit contains galactose and mannose, carob gum whose unit contains galactose and mannose, karaya gum which is a complex mixture of rhamnose, galactose and galacturonic acid, tragacanth gum which is a complex mixture of arabinose, galactose and galacturonic acid.

According to a preferred embodiment of the present invention, the polysaccharide alkyl ether is a derivative of guar gum, and, more particularly, ethylated guar having a degree of substitution of about 2 to 3, in particular 2.5, as described in RD 95378007 (October 1995).

The composition according to the present invention may contain, for example, a quantity of polysaccharide alkyl ether ranging from about 0.5 to 10%, and preferably from about 2 to 8% of the total weight of the composition.

The lipophilic active agent sensitive to oxygen and/or to water is present in the present composition in a quantity ranging from about 0.001 to 20%, preferably from about 0.01 to 5% and better still from about 0.2 to 1% of the total weight of the composition.

In the composition according to the present invention, there may be used any organic solvent capable of dissolving the lipophilic active agent sensitive-to oxygen and/or to water while preserving its good stability. The term "solvent" is understood and used herein to mean both hydrocarbon solvents and oils. The solvent may be chosen especially from fatty alcohols, fatty esters, oils of plant origin and/or mixtures thereof, as well as mixtures of these solvents with silicone and/or mineral oils. In particular, the solvent is one or more of aliphatic fatty alcohols having a straight or branched $C_{16}$–$C_{20}$ chain, diesters of a $C_6$–$C_{14}$ dicarboxylic acid and of isopropyl alcohol, triglycerides of a $C_6$–$C_{18}$ fatty acid and mixtures thereof.

Among the $C_{16}$–$C_{20}$ aliphatic fatty alcohols which may be used in the present invention, there may be mentioned 2-hexyldecanol such as that sold by the company Condea under the name "Isofol 16", octyl dodecanol such as that sold by the company Henkel under the name "Eutanol G", and isostearyl alcohol such as that sold by the company Sherex under the name "Adol 66".

Among the diesters of $C_6$–$C_{14}$ dicarboxylic acids and of isopropyl alcohol which may be used in the present invention, there may be mentioned diisopropyl adipate such as that sold by the company ISP under the name "Ceraphyl 230".

Among the triglycerides of $C_6$–$C_{18}$ fatty acids, according to the present invention, the use of mixed triglycerides of capric/caprylic acids, such as those sold by the company Hulls France under the name "Miglyol 812", is preferred.

In a specific embodiment of the present invention, it is possible to use the mixture of two or several of these solvents for the lipophilic active agent sensitive to oxygen and/or to water.

The composition according to the present invention may further contain all the ingredients conventionally used in the cosmetic or dermatological field, in usual concentrations. These ingredients are, in particular, one or more fatty substances, preservatives, vitamins and other active agents, gelling agents, perfumes, surfactants, water, antioxidants, fillers, screening agents, moisturizing agents and mixtures thereof.

The present composition may also contain ionic and/or nonionic type lipid vesicles. The quantities of these various adjuvants which may be used are those conventionally used in the cosmetic and/or dermatological fields, and for example about 0.01% to 20% of the total weight of the composition.

Other conventional constituents of cosmetic, pharmaceutical or veterinary compositions may be introduced into the emulsions according to the present invention. The nature of these ingredients and their proportion should, preferably, be compatible with the desired stability of the active agent sensitive to oxygen and/or to water in the compositions according to the invention.

The present composition may be provided in any of the galenic forms normally used for a topical application, especially in the form of an oily gel or an oil-in-water or water-in-oil emulsion. The composition may be fluid to a greater or lesser degree and may be in the form of a cream, an ointment, a paste or a foam, for example.

When the composition of the present invention is an emulsion, the proportion of the fatty phase may range from about 5 to 80% by weight, and preferably from about 5 to 50% by weight relative to the total weight of the composition. The oils, emulsifiers and coemulsifiers used in the composition in emulsion may be those conventionally used in the domain considered. The emulsifier and coemulsifier are present, in the composition, in a proportion ranging from about 0.3 to 30% by weight, and preferably from about 0.5 to 20% by weight relative to the total weight of the composition. The emulsion may, in addition, contain lipid vesicles.

As emulsifiers which can be used in the present invention, there may be mentioned, for example, the silicone emulsifiers, especially the polyoxyethylenated $C_{10}$–$C_{22}$ alkyl dimethicone copolyols such as cetyl dimethicone copolyol or "Abil EM-90", from the company Goldschmidt, or polyoxyethylenated and polyoxypropylenated lauryl dimethicone copolyol such as Q2-5200 from Dow Corning, and a mixture of the two.

Polyoxyethylenated dimethicone copolyols such as SP 1228 from General Electric and also Q2-3225 C from Dow Corning may also be used.

The oily phase of the emulsion may also contain an additional oil which is inert towards the active agent sensitive to oxygen and/or to water, preferably chosen from mineral or silicone oils.

Among the mineral oils which can be used according to the present invention, there may be mentioned, inter alia, isohexadecane, paraffin, isoparaffin and petroleum jelly.

Among the silicone oils which can be used in the present invention, there may be mentioned, inter alia, dimethicones, dimethiconols, cyclomethicones such as cyclopentadimethylsiloxane (or cyclomethicone D5) or cyclohexadimethylsiloxane (or cyclodimethicone D6) or alkyl dimethicones and a mixture of some of these compounds such as "Q2-1401 gum" from Dow Corning.

The present composition may be used especially for the treatment of the skin, in particular for treating acne and the damage induced by age and/or the sun, and more especially normal and/or small wrinkles and/or aging of the skin. Consequently, another object of the present invention is the cosmetic and/or dermatological use of the composition as defined above for treating acne and/or normal and/or small wrinkles and/or aging of the skin. By 'aging of the skin' is meant the general deterioration of skin appearance due to the passage of time, such as wrinkling, discoloration or blotching.

The present invention will now be further described by reference to certain examples which are provided solely for purposes of illustration and are not intended to be limitative. The quantities are given therein in % by weight.

EXAMPLE 1

| | |
|---|---|
| Retinol | 0.15% |
| Ethylated guar having a degree of substitution of about 2.5 | 4% |
| 2-hexyldecanol (Isofol-16) | qs 100% |

This gel may be used, in particular, for the treatment of acne.

EXAMPLE 2

This example differs from Example 1 in the use of Miglyol 812 in place of Isofol-16.

EXAMPLE 3

| Phase A: | |
|---|---|
| Abil EM-90 | 2% |
| Cyclomethicone D5 | 9.5% |
| Miglyol 812 | 10% |
| Q2 1401 gum | 4% |

| Phase B: | |
|---|---|
| Glycerin | 5% |
| Triethanoloamine | 0.2% |
| Deionized water | 61.3% |

| Phase C: | |
|---|---|
| Isofol 16 | 7.5% |
| Ethylated guar having a degree of substitution of about 2.5 | 2% |
| Retinol | 0.5% |

This cream, applied around the contour of the eyes as cure from 2 to 5 times per week, has the effect of smoothing the fine small wrinkles of the contour of the eye.

EXAMPLE 4

This example differs from Example 1 in the use of retinol palmitate instead of retinol.

Having described the present invention, it will be apparent to one skilled in the art that many changes and modification may be made to the above-described embodiments without departing from the spirit and scope of the present invention.

What is claimed as new and is desired to be secured by Letters: Patent of the United States is:

1. A stable gelled composition, comprising at least one lipophilic active agent sensitive to at least oxygen, and a solvent, which composition comprises, as gelling agent, at least ethylated guar gum.

2. The composition of claim 1, wherein the ethylated guar gum has a molecular weight of greater than about 100,000.

3. The composition of claim 1, wherein the ethylated guar gum is present in a quantity ranging from about 0.5 to 10% of the total weight of the composition.

4. The composition of claim 1, wherein the ethylated guar gum is present in a quantity ranging from about 2 to 8% of the total weight of the composition.

5. The composition of claim 1, wherein the lipophilic active agent sensitive to at least oxygen is retinol or compounds containing the active moiety of retinol, flavonoids or polyunsaturated fatty acids.

6. The composition of claim 5, wherein said compounds are selected from the group consisting of β-carotene, retinol acetate and retinol palmitate.

7. The composition of claim 1, wherein the lipophilic active agent sensitive to at least oxygen is present in a quantity ranging from about 0.1 to 5% of the total weight of the composition.

8. The composition of claim 1, wherein the solvent is selected from the group consisting of fatty alcohols, fatty esters, vegetable oils and mixtures thereof, as well as mixtures of these solvents with silicone or mineral oils or both.

9. The composition of claim 1, which is in the form of an oily gel, a water-in-oil emulsion or an oil-in-water emulsion.

10. The composition of claim 1, which is in a form of a cream, ointment, paste or foam.

11. The composition of claim 1, wherein the ethylated guar gum has a molecular weight of greater than about 200,000.

12. The composition of claim 1, wherein the ethylated guar gum is ethylated guar gum having a degree of substitution of about 2 to 3.

13. A method of stabilizing a lipophilic active agent which is sensitive to at least oxygen, which comprises adding to said lipophilic active agent a polysaccharide alkyl ether formed of units comprising at least two different glycoside rings, each unit comprising at least one hydroxyl group substituted with a saturated hydrocarbon alkyl group.

14. The method of claim 13, wherein the polysaccharide alkyl ether is an alkyl ether of a gum selected from the group consisting of guar gum, carob gum, karaya gum, tragacanth gum and mixtures thereof.

15. The method of claim 13, wherein said lipophilic active agent sensitive to at least oxygen is retinol or compounds containing the active moiety of retinol, flavonoids or polyunsaturated fatty acids.

16. The method of claim 15, wherein said compounds are selected from the group consisting of P-carotene, retinol acetate and retinol palmitate.

17. The method of claim 13, wherein said polysaccharide alkyl ether has a molecular weight of greater than 100,000.

18. The method of claim 17, wherein said polysaccharide alkyl ether has a molecular weight of greater than 200,000.

19. The method of claim 13, wherein the polysaccharide alkyl ether is ethylated guar gum having a degree of substitution of about 2 to 3.

20. A method of treating acne or wrinkles in mammalian skin, which comprises applying to skin of a mammal in need thereof an effective amount of a stable gelled composition, comprising at least one lipophilic active agent sensitive to at least oxygen, and a solvent which composition comprises, as a gelling agent, at least ethylated guar gum.

21. The method of claim 20, wherein said mammal is a human.

22. The method of claim 20, wherein said lipophilic active agent sensitive to at least oxygen is retinol or compounds containing the active moiety of retinol, flavonoids or polyunsaturated fatty acids.

23. The method of claim 22, wherein said compounds are selected from the group consisting of β-carotene, retinol acetate and retinol palmitate.

24. The method of claim 20, wherein said ethylated guar gum has a molecular weight of greater than 100,000.

25. The method of claim 24, wherein said ethylated guar gum has a molecular weight of greater than 200,000.

26. The method of claim 20, wherein the ethylated guar gum is ethylated guar gum having a degree of substitution of 2 to 3.

* * * * *